United States Patent
Gold et al.

[19]

[11] Patent Number: 5,921,233
[45] Date of Patent: Jul. 13, 1999

[54] LIQUID DISPENSER ASSEMBLY PARTICULARLY FOR MEDICAL APPLICATIONS

[75] Inventors: Scott Gold, New York; John V. Mizzi, Poughkeepsie, both of N.Y.

[73] Assignee: Pincgold LLC, New York, N.Y.

[21] Appl. No.: 08/923,151

[22] Filed: Sep. 4, 1997

[51] Int. Cl.[6] .......................... A61M 11/00; A61M 16/00; A61M 5/178; B65D 43/06
[52] U.S. Cl. ........................ 128/200.22; 128/200.14; 128/203.12; 128/203.28; 220/209; 220/324; 220/355; 220/720; 222/92; 222/211; 222/527; 222/528; 222/530; 222/542; 604/19; 604/37
[58] Field of Search .................... 128/200.14, 200.22, 128/203.12, 203.28; 220/500, 501, 505, 323, 324, 354, 355, 720; 222/72, 633, 92–96, 204, 527, 206–213, 528, 530, 542; 604/19, 37, 296, 298

[56] References Cited

U.S. PATENT DOCUMENTS

| | | |
|---|---|---|
| 238,388 | 3/1881 | Heine ........................................ 239/588 |
| 423,198 | 3/1890 | Windolph ............................ 128/200.14 |
| 790,318 | 5/1905 | Sams .................................... 128/200.14 |
| 2,115,959 | 5/1938 | Lewis .................................... 128/200.14 |
| 2,219,146 | 10/1940 | Beugmer . | |
| 2,331,117 | 10/1943 | Goodhue et al. ................... 128/200.14 |
| 2,449,125 | 9/1948 | King .................................... 128/200.14 |
| 3,529,774 | 9/1970 | Apri ..................................... 239/581.1 |
| 3,698,868 | 10/1972 | Bilichniansky . | |
| 4,474,312 | 10/1984 | Donoghue ............................... 222/205 |
| 4,930,997 | 6/1990 | Bennett .................................... 417/410 |
| 5,020,526 | 6/1991 | Epstein .............................. 128/200.14 |
| 5,041,881 | 8/1991 | Andris ..................................... 222/207 |
| 5,158,123 | 10/1992 | Senko ...................................... 141/338 |
| 5,312,009 | 5/1994 | Ratgiczak et al. ...................... 220/258 |
| 5,400,923 | 3/1995 | Golias et al. ............................. 222/82 |
| 5,505,193 | 4/1996 | Ballini and Merlin ............ 128/200.14 |
| 5,549,224 | 8/1996 | Wu et al. ................................. 222/158 |
| 5,570,820 | 11/1996 | Amoroal ................................. 222/205 |
| 5,624,062 | 4/1997 | Pedersen et al. ....................... 222/528 |
| 5,775,546 | 7/1998 | Buehler ................................... 222/209 |

OTHER PUBLICATIONS

Suction Devices; Thom Dick, *JEMS;* Mar. 1985, pp. 30–46.
"Pressurized Aerosol vs. Jet Aero. Del. . .", Fuller HD, Dolovich MB. . ., Am. Rev. Respir. Dis. 1990: 141:440–444.

*Primary Examiner*—Kimberly L. Asher
*Attorney, Agent, or Firm*—R. Neil Sudol; Henry D. Coleman

[57] ABSTRACT

A liquid dispenser assembly for medical applications includes a container holding a predetermined quantity of a therapeutic liquid in a storage chamber. The container has a wall or panel provided with a port. A dip tube is disposed in the chamber and extends from the port to a lower portion of the storage chamber. The disepnser assembly further includes a hollow compressible dispenser body. An applicator tube is attached at one end to the dispenser body and extends at a free end, i.e., an end opposite the dispenser body, into the dip tube. The applicator tube is removable from the dip tube after an expansion of the dispenser body from a collapsed configuration and a concomitant drawing of an aliquot of the liquid into the dispenser body through the dip tube and the applicator tube.

12 Claims, 2 Drawing Sheets

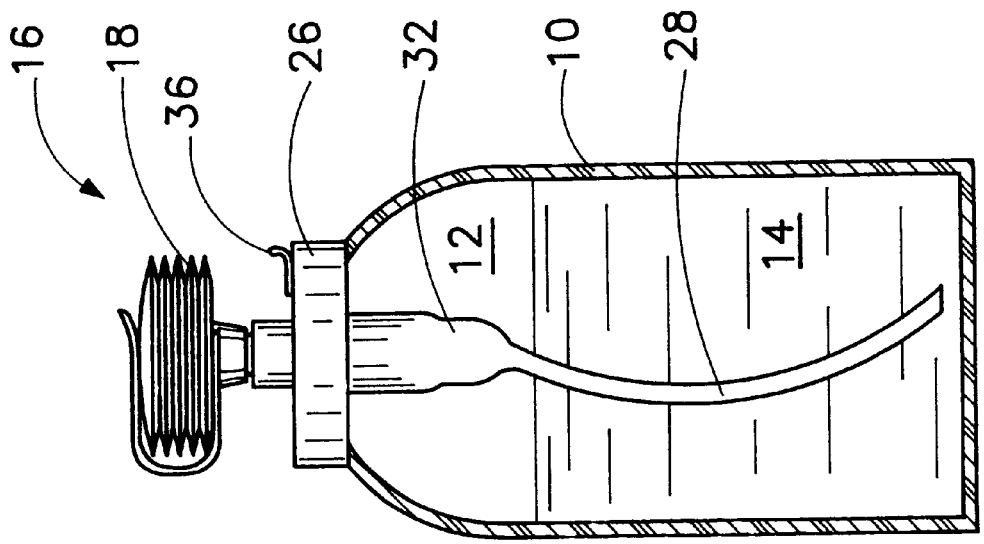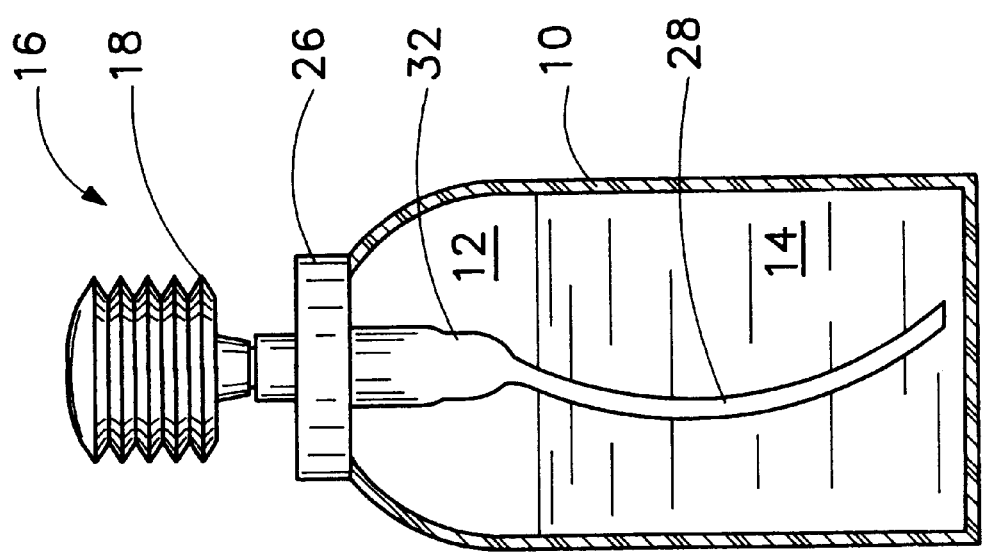

5,921,233

LIQUID DISPENSER ASSEMBLY PARTICULARLY FOR MEDICAL APPLICATIONS

BACKGROUND OF THE INVENTION

This invention relates to a liquid dispenser assembly. More particularly, this invention relates to a liquid spray dispenser assembly utilizable in irrigating nasal passages.

Spray dispensers for treating nasal passages are well known.

A particular use for nasal sprays is in cleaning nasal passages which have been subjected to surgery or other therapeutic procedure. The tissues at a surgical site are obviously prone to clotting and the aggregation of contaminants and possible infectious agents which may inhibit healing. A hand held nasal irrigation device for cleaning surgically treated nasal tissues would be of use to patients.

OBJECTS OF THE INVENTION

An object of the present invention is to provide a liquid dispenser assembly.

A more specific object of the present invention is to provide such an assembly wherein a hand-held device is used for applying a liquid spray.

An even more specific object of the present invention is to provide such a liquid spray assembly which is useful for spraying or irrigating nasal passages, for example, nasal passages which have been subjected to surgery and require periodic cleaning during a convalescent period.

Another object of the present invention is to provide a nasal irrigator with a replenishment reservoir for short-term personal use.

These and other objects of the present invention will be apparent from the descriptions and drawings herein.

SUMMARY OF THE INVENTION

A liquid dispenser assembly for medical applications comprises, according to the present invention, a container holding a predetermined quantity of a therapeutic liquid in a storage chamber, the container having a wall or panel provided with a port, a dip tube disposed in the chamber and extending from the port to a lower portion of the storage chamber, and a hollow compressible dispenser body. An applicator tube is attached at one end to the dispenser body and extends at a free end, i.e., an end opposite the dispenser body, into the dip tube. The applicator tube is removable from the dip tube after an expansion of the dispenser body from a collapsed configuration and a concomitant drawing of an aliquot of the liquid into the dispenser body through the dip tube and the applicator tube.

According to another feature of the present invention, the dip tube is resilient in a portion thereof disposed proximately to the port. The resilience of the dip tube is such as to facilitate an effectively liquid-tight engagement between the free end of the applicator tube and the dip tube. Preferably, the applicator tube is provided at its free end with an enlarged terminal element or nozzle, the terminal element forming the liquid-tight engagement with the dip tube. Also, it is contemplated that the applicator tube is deformable to assume different shapes, thereby enhancing the versatility of use.

The dispenser body may take the form of a bellows. During shipping, the bellows may be stored in a collapsed configuration by a restraining clip attached thereto.

According to a further feature of the present invention, the container is provided with a check valve for relieving an underpressure in the container.

In a dispenser assembly in accordance with the present invention, the storage of the applicator nozzle inside the liquid container in a docking relationship protects the applicator nozzle from contamination. The insertion of the applicator tube into the dip tube facilitates the withdrawal of fluid from the storage container.

A liquid dispenser assembly in accordance with the present invention is easy to manufacture and of simple construction.

The liquid stored in the container may be sterile and the container disposable for preventing the introduction of possibly contaminated liquid into the container for spray dispensing with the dispenser body and applicator tube.

BRIEF DESCRIPTION OF THE DRAWINGS

FIG. 1 is a side elevational view, partly in cross-section, of a nasal irrigator assembly in accordance with the present invention, showing a dispenser member in the form of a bellows in an expanded configuration atop a replenishment container.

FIG. 2 is a view similar to FIG. 1 showing the bellows dispenser member in a collapsed storage and transport configuration.

DESCRIPTION OF THE PREFERRED EMBODIMENTS

Figure 4:
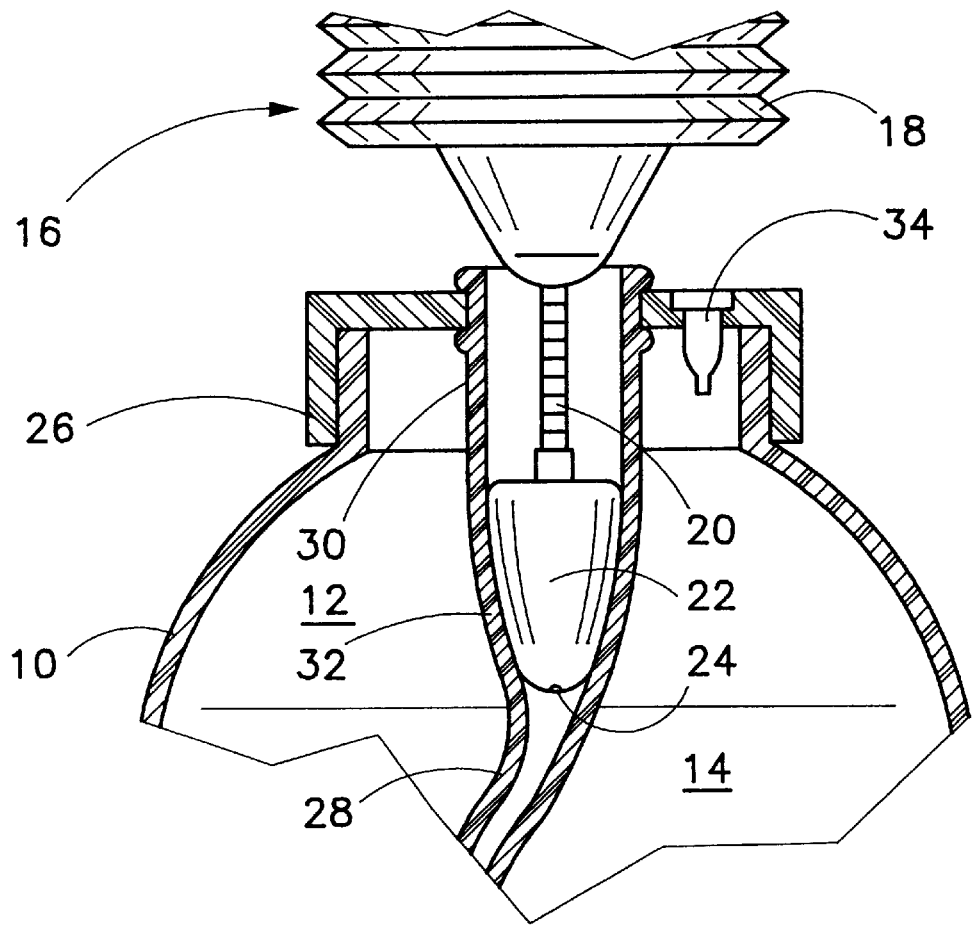
FIG. 4 is a partial cross-sectional view, on an enlarged scale, showing the mating of the applicator tube with a dip tube inside the container.

As shown in the drawings, a liquid dispenser assembly particularly useful in the irrigation of nasal passages, for example, to clean olfactory tissues after nasal surgery, comprises a container 10 defining a storage chamber 12 which holds a reservoir of liquid irrigant 14 such as a sterile saline solution. The saline solution may contain various additives such as antibiotics, anti-inflammatory agents, topical anesthetics, etc.

Figure 3:
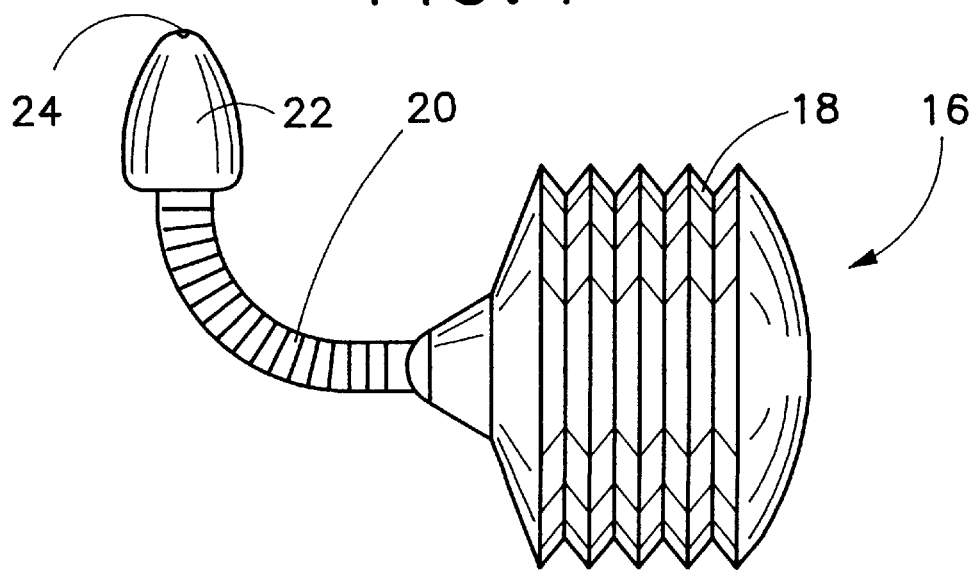
FIG. 3 is a side elevational view of the bellows dispenser member, showing an applicator tube in a bent configuration for use in nasal irrigation.

The nasal irrigator assembly further comprises a hand actuatable dispenser 16, shown separately in FIG. 3. Dispenser 16 includes a compressible receptacle or body member 18 in the form of a bellows. Bellows 18 is made of polymeric material and is biased by internal spring forces to assume an expanded configuration (FIGS. 1 and 3) having a volume of about 50 cc, sufficient for the irrigation of two nostrils. To bellows 18 is attached a deformably bendable (e.g., corrugated) neck element or applicator tube 20. At a free end, opposite bellows 18, applicator tube 20 is provided an enlarged terminal or nozzle element 22 having an outlet aperture 24. FIG. 3 shows dispenser 16 with applicator tube 20 in a bent configuration for faciltiating the insertion of terminal or nozzle element 22 into a user's nostril.

Container 10 is provided with a cap 26 to which a dip tube 28 is attached. More specifically, an upper end of dip tibe 28 is inserted in an opening or port 30 in cap 26. Dip tube 28 extends from cap 26 to a lower end of chamber 12. At an upper end, proximately to cap 26 and port 30, dip tube 28 is integrally formed with a socket portion 32 for receiving terminal or nozzle element 22. Preferably, dip tube 26, particularly socket 32, is made of a flexible or resilient thermoplastic elastomer such as silicone or polyurethane, facilitating a substantially air tight seal between nozzle element 22 and socket 32 upon an insertion of the nozzle element through port 30 into the socket, as shown particularly in FIG. 4.

As illustrated in FIG. 4, cap 26 is provided with a check valve 34 for relieving underpressure generated in container 10 by use of the dispenser assembly. A removable seal 36 (FIG. 2) may be adhesively attached to cap 26 over check valve 34 during shipping. Preferably, cap 26 is permanently attached to container 10 to at least discourage, if not prevent, refilling of container 10, thereby minimizing or avoiding contamination problems.

As shown in FIG. 2, the dispenser assembly is shipped with a disposable retaining clip 38 disposed about bellows 18 for maintaining that element in a collapsed configuration. With bellows 18 in the collapsed configuration of FIG. 2, the entire dispenser assembly is more compact, which makes shipping more efficient.

In using the dispenser assembly described herein, bellows 18 is permitted to expand in response to internal spring stresses from a collapsed configuration while applicator tube 20 and nozzle element 22 are disposed in socket 32. That expansion generates a vacuum serving to draw liquid from reservoir 14 through dip tube 28 and applicator tube 20 into bellows 18. After bellows has expanded to draw an aliquot of liquid into itself, bellows 18 is grasped and pulled away from container 10, thereby withdrawing applicator tube 20 and nozzle element 22 from socket 32 and through port 30. Applicator tube 20 is then bent to a desirable configuration, for example, as shown in FIG. 3, for facilitating the insertion of nozzle element 22 into a nostril and the manual squeezing of bellows 18 to eject the liquid therein through applicator tube 20 and nozzle element 22 into the nostril. Nozzle element 22 is designed to produce a spray pattern, atomizing the liquid in small droplets.

After use of the dispenser assembly to perform a nasal irrigation procedure as described herein, applicator tube 20 is straightened and inserted back into socket 32 for storage (see FIGS. 1 and 4). Clip 36 may be reapplied to retain bellows 18 in the collapsed configuration of FIG. 2, if necessary, for example, to fit the dispenser assembly into a medicine cabinet.

Generally, the liquid in reservoir 14 can be a sterile saline solution, including, for instance, sodium bicarbonate. Of course, various other additives may be included in the irrigant, such as antibacterial components and fragrances.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A liquid dispenser assembly for medical applications, comprising:
    a container holding a predetermined quantity of a therapeutic liquid in a storage chamber, said container having a wall or panel provided with a port;
    a dip tube disposed in said chamber and extending from said port to a lower portion of said storage chamber;
    a hollow compressible dispenser body; and
    an applicator tube attached at one end to said dispenser body and extending at an opposite end into said dip tube, said applicator tube being removable from said dip tube after an expansion of said dispenser body from a collapsed configuration and a concomitant drawing of an aliquot of said liquid into said dispenser body through said dip tube and said applicator tube.

2. The assembly defined in claim 1 wherein said dip tube is resilient in a portion thereof disposed proximately to said port, for facilitating an effectively liquid-tight engagement between said opposite end of said applicator tube and said dip tube.

3. The assembly defined in claim 2 wherein said applicator tube is provided at said opposite end with an enlarged terminal element, said terminal element forming said liquid-tight engagement with said dip tube.

4. The assembly defined in claim 3 wherein said applicator tube is deformable to assume different shapes.

5. The assembly defined in claim 4 wherein said dispenser body takes the form of a bellows.

6. The assembly defined in claim 5 wherein said container is provided with a check valve for relieving an underpressure in said container.

7. The assembly defined in claim 5 wherein said bellows is provided with a restraining clip attached to said bellows for temporarily maintaining said bellows in a collapsed configuration.

8. The assembly defined in claim 1 wherein said applicator tube is provided at said opposite end with an enlarged terminal element, said terminal element forming an effectively liquid-tight engagement with said dip tube.

9. The assembly defined in claim 1 wherein said applicator tube is deformable to assume different shapes.

10. The assembly defined in claim 1 wherein said dispenser body takes the form of a bellows.

11. The assembly defined in claim 1 wherein said container is provided with a check valve for relieving an underpressure in said container.

12. The assembly defined in claim 1 wherein said dispenser body is provided with a restraining clip attached to said dispenser body for temporarily maintaining said dispenser body in a collapsed configuration.

\* \* \* \* \*